United States Patent [19]

Schultz et al.

[11] 4,326,516
[45] Apr. 27, 1982

[54] INTRACATHETER-INTRAVENOUS TUBING LOCK

[76] Inventors: Kenneth E. Schultz, 402 NW. 94th La., Coral Springs, Fla. 33060; Mary Craycraft, 6820 SW. 43rd Ct., Davie, Fla. 33314

[21] Appl. No.: 109,132

[22] Filed: Jan. 2, 1980

[51] Int. Cl.³ .............................................. A61M 5/00
[52] U.S. Cl. ............................ 128/214 R; 128/214.4
[58] Field of Search ........... 128/215, 216, 221, 214 R, 128/214.2, 214.4; 403/330; 285/311, 312, 320; 24/245 A, 246

[56] References Cited

U.S. PATENT DOCUMENTS

| | | | |
|---|---|---|---|
| 342,638 | 5/1886 | Ross | 24/246 |
| 435,450 | 9/1890 | Richards | 24/246 |
| 839,226 | 12/1906 | Sturm et al. | 24/246 |
| 844,679 | 2/1907 | Karle | 24/246 |
| 1,524,242 | 1/1925 | Hein | 128/221 |
| 2,278,074 | 3/1942 | Hauf | 285/320 |
| 2,389,355 | 11/1945 | Goland et al. | 128/214.4 |
| 3,658,061 | 4/1972 | Hall | 128/214.4 |
| 3,672,367 | 6/1972 | Scislowicz | 128/214.4 |
| 3,709,223 | 1/1973 | Macalalad et al. | 128/214.4 |
| 3,809,081 | 5/1974 | Loveless | 128/214.4 |
| 4,123,091 | 10/1978 | Costentino et al. | 128/214.4 |
| 4,137,916 | 2/1979 | Killman et al. | 128/214.4 |
| 4,144,885 | 3/1979 | Stait | 128/234 |
| 4,191,186 | 3/1980 | Keeler | 128/214.4 |
| 4,230,109 | 10/1980 | Geiss | 128/214 |
| 4,231,367 | 11/1980 | Rash | 128/214.4 |

FOREIGN PATENT DOCUMENTS

| | | | |
|---|---|---|---|
| 38483 | 6/1931 | France | 24/246 |
| 1506163 | 6/1974 | United Kingdom | 128/214 R |

*Primary Examiner*—Robert W. Michell
*Assistant Examiner*—Nancy A. B. Swisher
*Attorney, Agent, or Firm*—Wigman & Cohen

[57] ABSTRACT

A releasable device for securely fastening intravenous tubing to an intracatheter insert or needle and method are disclosed. The securing system comprises a locking member attached to the hub of the intracatheter insert and a projection knob molded near the end of the intravenous tubing, as part of the tubing. The locking member comprises a loop portion which is designed to securely but releasably fit over and around the projection knob when the intravenous tubing is inserted into position in the intracatheter insert. The locking member is also comprised of a pair of inclined arms attached to the loop portion and to which is attached a pair of parallel legs further including a pair of radially inwardly directed hinge pins, which hinge pins are hingedly attached to the hub of the intracatheter insert or needle. The locking member of the present invention is preferably constructed of a single length of metal rod which is bent into the desired shape.

11 Claims, 2 Drawing Figures

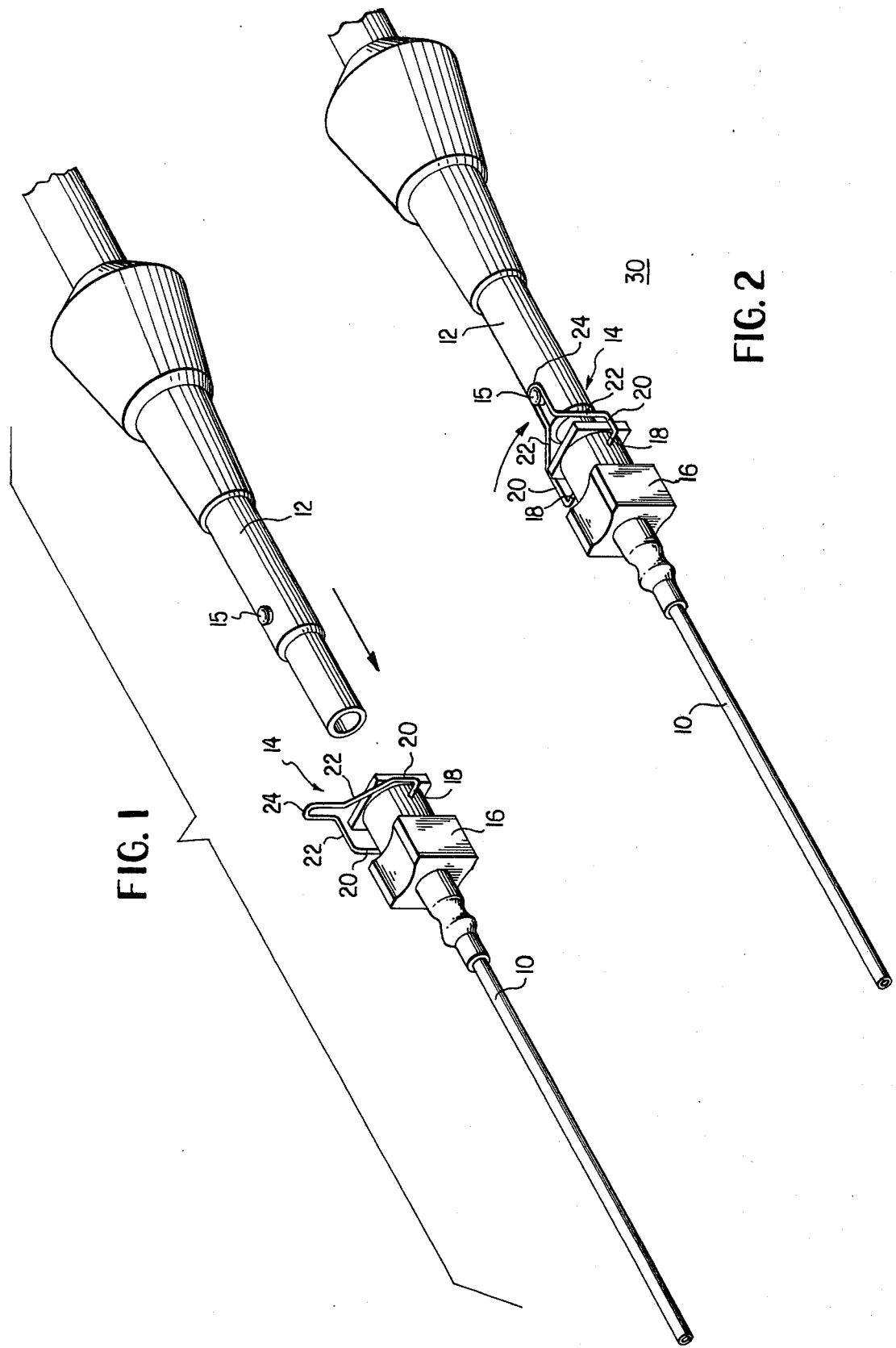

INTRACATHETER-INTRAVENOUS TUBING LOCK

BACKGROUND OF THE INVENTION

The present invention relates generally to releasable tubing connections used in intravenous feeding, and more particularly to a locking device adapted to prevent separation of a hub member from a piece of tubing in an intracatheter-intravenous tubing assembly.

The most common method of intravenous feeding requires the installation of a long tapered insert into a vein with the aid of a hypodermic needle. The insert, which is conventionally formed of plastic or other flexible material, is first installed over the needle, and then inserted into a vein. Once in place, the needle is withdrawn, leaving the insert in place. Intravenous supply tubing is then connected to the insert. Because the insert must be installed in the vein independently, the connection between intravenous supply and the insert cannot be permanent. The most common means for effecting the connection generally provides for the insertion of the forward end of the intravenous supply line into the back of the insert tube, with the connection being maintained by friction. A difficulty with this type of standard connection is the potential for separation, due for example, to patient movement, thus allowing intravenous fluid and the patients blood to soil bedclothes. Temporary interruption of the nutrient supply, or loss of blood, might also pose a serious health risk to the patient.

Others have recognized the need for a securing device that will maintain the connection in an intracatheter-intravenous tubing assembly, even with patient movement. One such device is disclosed in U.S. Pat. No. 4,082,094 which shows a locking device which is provided with a channel adapted to receive the conventional tubing connection between a tapered vein insert tube and a cooperating connector at the termination of an intravenous supply tube. The tubing connection is placed in this channel, and transverse compression applied, with the result that the tubing connection is held in the body so as to prevent separation. One of the problems with this type of device is that the tubing must be pulled from it, with the attendant possibility of separation of the tubing connection. A further drawback of this device is that it is separate from the tubing assembly itself, and thus is required to be carried by the person who is to apply it to the tubing. It is also another device to be maintained in the inventory of a hospital, among the many other thousands of items so stocked by a hospital.

Another tubing connector device is disclosed in U.S. Pat. No. 4,123,091 which shows a coupling comprised of a first connector body, consisting of a central male tube-shaped member which is provided with grooves extending around the longitudinal end thereof in order to form slots for "O" rings. These "O" rings act to provide a liquid-tight seal between the connector bodies. In addition, a pair of flanged members is formed as part of the first connector body and engages a recessed collar member in order to prevent the disengagement of the connector bodies. One of the drawbacks with this type of connector is that it requires two hands to operate, which might not always be possible under certain conditions, especially in emergency situations. Another disadvantage is that the "O" rings form a ribbing on the tubing, and the disengagement of the tubing could very likely cause excessive movement of the intracatheter insert in the patient's arm. Such movement is likely to cause patient discomfort, blockage of the flow of nutrients to the patient, and may also cause the insert to come out of the patient's vein and possibly even the patient's limb.

Another example of a ribbed-type connector is that of U.S. Pat. No. 4,133,312. This type of connector has all of the disadvantages of the connector previously described.

In the past, various other types of devices have been known for use in holding intravenous needles. U.S. Pat. Nos. 3,167,072 and 3,900,026 show two such holding devices. These devices are directed towards holding the intravenous injection needle in the patient's arm, rather than maintaining the intracatheter-intravenous tubing connection.

Although not considered relevant to the present invention various types of couplings have been used in connection with hoses in general. Thus, for example, U.S. Pat. No. 1,148,913 discloses a coupling equipped with a pivoted locking means for use in sealing the joint between a male and female member of the coupling, thus ensuring the joint against leakage or accidental disconnection. U.S. Pat. No. 2,494,774 discloses a telescopically engageable coupling utilizing a pivotable latching device for securing a hose coupling.

It is also known, as disclosed in U.S. Pat. No. 4,045,058, to use elastic straps containing uniformly spaced holes for securing two tubes together. The second tube has attached thereto a collar with buttons over which are fastened the respective elastic straps. This maintains the coupling of the two tubes effectively preventing their disengagement.

In light of the above-disclosed prior art devices, it is therefore obvious that a need exists for a releasable means already secured to an intracatheter device and intravenous tubing to secure the connection and disconnection therebetween without excessive pulling or twisting.

SUMMARY OF THE INVENTION

The intracatheter-intravenous tubing securing device of the present invention is an economical, convenient and easy to use device which can be rapidly and reliably employed to prevent unwanted separation of the intracatheter insert from the intravenous tubing attached thereto. The securing device comprises a knob projecting from the intravenous tubing proximate to the end of said tubing to be inserted into the connector of an intracatheter insert or needle and a locking member pivotably attached to the connector of the intracatheter insert for placement over the knob to thereby lock the intravenous tubing to the intracatheter insert or needle. In further detail, the locking member comprises a pair of parallel legs pivotably attached to the hub, a pair of inclined arms respectively attached to the pair of parallel legs and a loop portion attached to the pair of inclined arms and constructed so as to be placed over the knob projecting from the intravenous tubing. The locking member is pivotably attached to the connector of the intracatheter insert by means of radially inwardly directed pins, each of which is attached to a respective one of the pair of parallel legs. The knob projecting from the intravenous tubing may be advantageously molded together with the tubing at the time of its manufacture. The loop portion of the locking member is constructed to fit snugly over the projecting knob, yet due to its slight flexibility and the resiliency of the projecting knob, it is easily released from said knob when it is desired to remove the intravenous tubing from the intracatheter insert.

OBJECTS OF THE INVENTION

It is therefore an object of the present invention to improve the operability and reliability of intracatheter-intravenous tubing securing means.

Another object of the invention is to provide a compact device for releasably securing intravenous tubing to an intracatheter insert.

A further object is to provide a low cost yet effective intracatheter-intravenous tubing securing means which is self-contained on said intracatheter insert and said intravenous tubing.

Another object of the invention is to provide a simple yet improved method of securing intravenous tubing to an intracatheter insert or needle.

Other objects, advantages and novel features of the invention will be apparent from a reading of the following detailed description when considered in conjunction with the accompanying drawings.

BRIEF DESCRIPTION OF THE DRAWINGS

FIG. 1 is a prospective view of an intracatheter insert and intravenous tubing utilizing the present invention, before the tubing is joined to the insert.

FIG. 2 is a prospective view showing the intracatheter-intravenous tubing securing means in a locked position immediately after the engagement of the tubing in the intracatheter insert.

DETAILED DESCRIPTION OF A PREFERRED EMBODIMENT

Referring now in detail to the drawings, wherein like numerals indicate like elements throughout the several views, FIG. 1 illustrates an intracatheter insert 10 and an intravenous tube 12 for connection thereto, prior to their actual connection. Both the intracatheter insert or needle 10 and the intravenous tubing 12 may be of conventional construction with the exception of the addition of the locking member 14 attached to the intracatheter insert 10 and the knob 15 molded as part of the intravenous tubing. Because the intracatheter insert 10 and the intravenous tubing 12 are conventional, with the exception of the addition of the instant invention, as described above, neither will be described in any further detail. The locking member 14 of the present invention is pivotably attached, as will further be described herein below, to the metal connector 16 of the intracatheter insert or needle 10. The locking member 14 is preferably constructed of a thin metal rod, such as steel, and is pivotably attached to the connector 16 by means of radially inwardly directed pins 18 attached therethrough. Prior to its attachment to the connector 16, the locking means 14 is bent into the shape as described herein.

The locking means 14 is also constructed to comprise a pair of parallel legs 20 attached to the pins 18 and to which parallel legs 20 a pair of inclined arms 22 is attached. The remaining portion of the locking member 14 is comprised of a loop portion 24 which is connected to the pair of inclined arms 22. As should be readily apparent to one of ordinary skill in the art, the locking member 14 is constructed of a single piece of rod stock, and bent into the shape as described above. The loop 24 is constructed to fit snugly over the rounded projection knob 15 which is molded or attached to the end of the intravenous tubing 12. Obviously, the locking member 14 can be pivotably attached to the intravenous tubing 12 by a suitable method and the rounded projection knob 15 can be located on the intracatheter insert 10 in a suitable manner.

FIG. 2 illustrates an intracatheter-intravenous tubing assembly 30 in its operational position embodying the locking member 14 and projection knob 15 of the present invention. In contrast to the perspective view of FIG. 1, in which the locking system is shown in its unengaged or open position, the perspective view of FIG. 2 illustrates the closed or locked position of the tubing lock of the present invention. As can readily be seen, the intravenous tubing 12 has been inserted into the connector 16 of the intracatheter insert 10 such that the loop 24 of the locking member 14 can be snugly fit over the projection knob 15. As has been previously described, the intravenous tubing 12 can be formed of any suitable material such as plastic or the like, making it resilient. Since the knob 15 is preferably molded as part of the intravenous tubing 12 during its production, it too has resilient characteristics. This allows for the easy release of the loop 24 of the locking member 14 from its closed position around the projection knob 15. Thus, it is possible and indeed very likely, that the instant locking system can be engaged and disengaged by one hand of the operator thereof. Indeed, the locking system of the present invention is so designed.

In operation, the intravenous tubing 12 is inserted into the connector 16 of the intracatheter insert 10 and the loop 24 of the locking member 14 is pushed down over, such that it surrounds the projection knob 15. In this position, it is not possible for the intracatheter-intravenous tube assembly 10 to become disengaged, unless a nurse or like person raises the loop 24 from its closed position surrounding the projection knob 15. Thus, even though the patient's limb may move, the assembly 30 will remain in its secured position as illustrated in FIG. 2.

There has been thus described a novel yet inexpensive locking system and method for releasably yet securely fastening intravenous tubing to an intracatheter insert or needle. Because of its construction, and its extremely low cost, the locking system of the present invention if desired, may be disposable along with the intracatheter insert or intravenous tubing to which it is attached and/or molded. With such construction, the locking system of the present invention is always immediately ready for use, whenever an IV tube is connected to an intracatheter insert. In addition, there are no additional items for a hospital to keep in stock, since the locking system of the present invention is constructed as part of the assembly it is designed to secure. Many modifications of the present securing system and variations of the present method of its use are possible in light of the above teachings and within the purview of the appended claims, without departing from the spirit and intended scope of the invention.

What is claimed is:

1. In an intravenous supply tubing having a connector and an intracatheter insert portion, a locking device for releasably securing said intravenous supply tubing to said intracatheter insert connector, comprising:

a knob projecting from said intravenous supply tubing proximate said connector of said intracatheter insert when said intravenous supply tubing and said intracatheter insert are in an operating position; and locking means pivotably attached at one end to said connector of said intracatheter insert to pivot about an axis which intersects the longitudinal axis of at least one of said intravenous supply tubing and said intracatheter insert substantially at a right angle for placement over said knob to thereby secure said intravenous supply tubing to said intracatheter insert.

2. In an intravenous supply tubing having a connector and an intracatheter insert portion, a locking device for releasably securing said intravenous supply tubing to said intracatheter insert connector, comprising:

locking means pivotably attached to one of said intravenous supply tubing and said intracatheter insert to pivot about an axis which intersects the longitudinal axis of at least one of said intravenous supply tubing and said intracatheter insert substantially at a right angle; and a knob attached to one of said intravenous supply tubing and said intracatheter insert, whereby when said intravenous supply tubing and said intracatheter insert are in an operating position, placement of said locking means over said knob secures together said intravenous supply tubing to said intracatheter insert.

3. The releasable locking device of claim 2, wherein said locking means comprises:

(a) a pair of parallel legs hingedly attached to said hub;

(b) a pair of inclined arms respectively connected to said pair of parallel legs; and (c) a loop portion connected to said pair of inclined arms and constructed to be placed over and around said knob projecting from said intravenous tubing.

4. The releasable locking device of claim 3, wherein said locking means further includes a pair of radially inwardly directed hinge pins, each connected to a respective one of said pair of parallel legs, for hingedly associating said locking means with said hub of said intracatheter insert.

5. The releasable locking device of claim 2, wherein said projecting knob is formed as an integral portion of said intravenous tubing.

6. The releasable locking device of claim 2, wherein said locking device is comprised of steel.

7. The releasable locking device of claim 2, wherein said loop portion of said locking means fits snugly over said projecting knob.

8. The locking device of claims 1 or 2 wherein:
said locking means may be released from its operating position by one hand of the operator thereof.

9. A method of releasably securing intravenous supply tubing to an intracatheter insert each of said supply tubing and said insert having one of a connector and a projecting knob, said connector including locking means pivotably attached thereto, said method comprising the steps of:

joining said intravenous supply tubing to said intracatheter insert by inserting one of said intravenous supply tubing and said intracatheter insert into said connector;

pivoting said locking means about an axis which intersects the longitudinal axis of one of said intravenous supply tubing and said intracheter insert at a right angle; and placing said locking means over and around said projecting knob such that said intravenous supply tubing is releasably secured to said intracatheter insert.

10. The method of claim 9, wherein said locking means further includes a pair of radially inwardly directed hinge pins, each connected to a respective one of said pair of parallel legs, for hingedly associating said locking means with said hub of said intracatheter insert.

11. The method of claim 9, wherein said loop portion of said locking means fits snugly over said projecting knob.

* * * * *